United States Patent [19]

Belanger et al.

[11] Patent Number: 4,537,906

[45] Date of Patent: Aug. 27, 1985

[54] SUBSTITUTED PHENYLALKENOIC ACIDS AND ESTERS

[75] Inventors: Patrice C. Belanger, Dollard des Ormeaux; John W. Gillard, Pointe Claire, both of Canada

[73] Assignee: Merck Frosst Canada, Inc., Quebec, Canada

[21] Appl. No.: 446,909

[22] Filed: Dec. 6, 1982

[51] Int. Cl.³ .................. C07C 69/76; A01N 37/00
[52] U.S. Cl. ..................... 514/532; 514/541;
514/568; 514/570; 514/576; 548/532; 549/230;
260/465 K; 562/459; 562/492; 560/51; 560/59;
560/102
[58] Field of Search ............ 560/492, 102, 51, 59;
514/532, 541, 570, 576; 548/532; 549/230;
562/459, 492

[56] References Cited

U.S. PATENT DOCUMENTS 3,859,338  1/1975  Engel et al. .................. 562/492

FOREIGN PATENT DOCUMENTS 0020230  10/1980  European Pat. Off. ............ 562/492

OTHER PUBLICATIONS

Franke, A. et al., Helvelica Chemica Acta, vol. 58, pp. 278–283, 1975.

*Primary Examiner*—Paul J. Killos
*Attorney, Agent, or Firm*—Alice O. Robertson; Daniel T. Szura

[57] ABSTRACT

Substituted phenylalkenoic acids and esters of the formula:

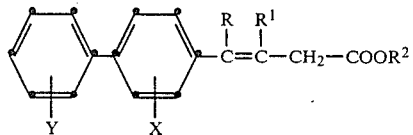

having useful pharmaceutical activity are disclosed.

8 Claims, No Drawings

SUBSTITUTED PHENYLALKENOIC ACIDS AND ESTERS

BACKGROUND OF THE INVENTION

The present invention is concerned with certain biphenylyl alkenoic acids and esters having pharmaceutical utility, especially for inhibiting blood platelet aggregation.

Biphenylylalkenoic acids where the alkenoic acid moiety has four or less carbon atoms are known (see e.g. European Patent Application No. 20230, German No. 2,205,732, RD No. 189,021, Belgian No. 840,354, Belgian No. 825,643). The trans isomer of biphenylylbutenoic acid is specifically taught in R. C. Child et al. Arznei Forsch 30, 695–702 (1980). These compounds are generally taught to have anti-inflammatory activity.

Biphenylyl alkenoic acids have been discovered which can be used as blood platelet aggregation inhibitors and to prevent bronchoconstriction.

SUMMARY OF THE INVENTION

Biphenylylalkenoic acids and esters of the formula:

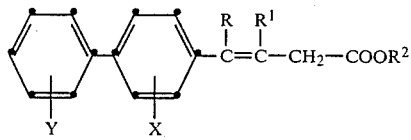

having the cis configuration and the use of cis biphenylylalkenoic acids as pharmaceuticals.

DETAILED DESCRIPTION OF THE INVENTION

The invention is embodied in the cis isomer of a compound having the formula

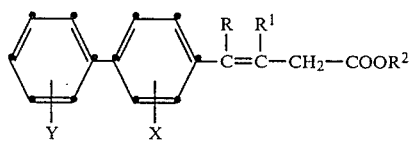

wherein
R is H or $C_1$–$C_4$ alkyl,
$R^1$ is H or $C_1$–$C_4$ alkyl,
$R^2$ is (i) hydrogen, (ii) $C_1$–$C_6$ alkyl,

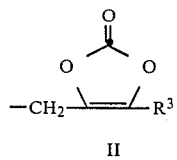

wherein $R^3$ is $C_1$–$C_6$ alkyl or aryl (as defined in U.S. Pat. No. 4,342,693); or

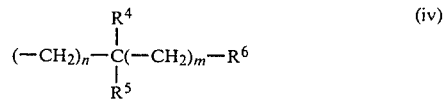

wherein
n is 0, 1, 2 or 3;
m is 0, 1, 2 or 3;
$R^4$ and $R^5$ are individually H or alkyl of 1 to 3 carbon atoms; and
$R^6$ is selected from the group consisting of
 (A) a monocyclic or bicyclic heterocyclic radical containing from 3 to 12 nuclear carbon atoms and 1 or 2 nuclear hetero atoms selected from N and S with at least one being N, and with each ring in the said heterocyclic radical containing 5 to 6 members and
 (B) the radical X-$R^7$ wherein X is —O—, —S— or —NH— and $R^7$ contains up to 21 carbon atoms and is (1) a hydrocarbon radical or (2) an acyl radical of an organic acyclic or monocyclic carboxylic acid containing not more than 1 hetero atom in the ring,
Y is H, halo, azido, $C_1$–$C_4$alkoxy, carboxy or $C_1$–$C_6$ alkyl; and
X is H, halo, azido, $C_1$–$C_4$alkoxy, carboxy or $C_1$–$C_6$alkyl
and pharmaceutically acceptable salts thereof.

The pharmaceutically acceptable salts are salts of the formula I acids with suitable bases, exemplified by the ammonium salts, the alkali metal salts e.g., sodium, potassium, the alkaline earth metal salts e.g. Ca, Mg and salts of amines such as lysine, morpholine, piperazine and the like.

The $C_1$–$C_4$ alkyl group substituents are exemplified by $CH_3$, t-butyl, isopropyl and the like. The $C_1$–$C_6$ alkyl group substituents are exemplified by $CH_3$, n-hexyl, sec.-butyl, isopropyl, t-butyl and the like. The halo substituent is Cl, Br, or F.

Identification and introduction of the formula II ester group is taught in U.S. Pat. No. 4,342,693, whose disclosure to the extent necessary is incorporated herein by reference. A preferred method for preparing a formula II group ester is by treating the lithium or silver salt of the formula I acid with the bromo derivative

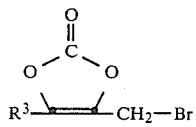

in a suitable reaction medium. Methyl, t-butyl and phenyl are preferred $R^3$ definitions.

Identification and introduction of the formula III ester group is taught in U.S. Pat. No. 3,983,138 and U.S. Pat. No. 3,988,341 and, to the extent necessary, these disclosures are incorporated herein by reference. Preferred formula III ester groups are those where $R^6$ is (i.) X-$R^7$ where X is O, S or NH and $R^7$ is hydrocarbyl or non-heterocyclic acyl or (ii) glutarimido, nicotinamido, phthalimido, naphthalimido, acetamido, maleimido or succinimido.

More preferred formula III ester groups are those having the formulae:

$-CH_2-R^8$, $-CH(CH_3)-R^8$ or $-(CH_2)_2-R^8$

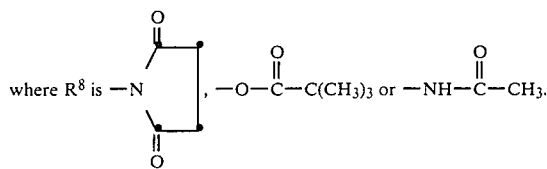

where $R^8$ is ...

Preferred compounds are those of formula I where $R^2$ is H. A more preferred group of compounds is formula I where $R^2$ is H and $R/R^1$ are independently selected from H and $CH_3$.

Another more preferred group of compounds is formula I where R, $R^1$ and $R^2$ are all H. A most preferred compound is formula I where X, Y, R, $R^1$ and $R^2$ are all H.

The compounds of Formula I (the cis trans isomers) are useful as pharmaceuticals.

Representative compounds inhibit bronchoconstriction induced by leukotrienes (LTD$_4$) or arachidonic acid—and in the latter instance, show no concomitant fall in blood pressure due to inhibition of synthesis of prostaglandin $I_2$ and $E_2$. Thus, the present compounds are considered to have thromboxane synthetase (TS) enzyme and cyclooxygenase (CO) enzyme inhibiting properties. A discussion of the metabolic cycle involving these enzymes is found in U.S. Pat. No. 4,233,778.

By virtue of the pharmacological activities of the formula I compounds, they are useful as cardiovascular agents, e.g., to treat and prevent blood platelet aggregation and to treat asthma.

For use as blood platelet aggregation inhibitors the present cis isomer compounds are administered either orally or parenterally in daily dosages ranging from 5 mg. to 1350 mg.

For use in treating asthma, the present compounds are administered orally, parenterally or by insufflation. The oral or parenteral daily dosage will range from 20 mg. to 1.500 mg. Administration by insufflation e.g. spray, will be in metered doses ranging from about 50 to about 1000 mcg per dose, administered as needed.

Appropriate dosage forms will be used. Suitable oral dosage forms are tablets, elixirs, solutions, emulsions, capsules and the like. Suitable parenteral dosage forms are solutions, emulsions and the like. Suitable insufflation dosage forms are sprays, aerosols and the like. The dosage forms are prepared using conventional procedures and, where required, pharmacologically acceptable diluents, carriers and the like.

The cis compounds of formula I can be prepared by any convenient method.

One such process involves the reaction of a biphenylyl aldehyde with a triphenyl phosphine alkenoic acid adduct in the presence of a coupling agent such as BuLi or a base such as $K_2CO_3$ activated by a Crown Ether like 18-Crown-6 as illustrated by the following equation:

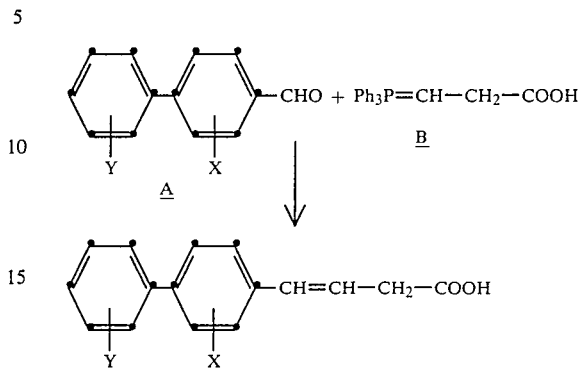

This reaction is generally carried out in a suitable solvent such as tetrahydrofuran or a like aprotic solvent at below 0° C. and preferably about −50° to −80° C. for n-BuLi catalyzed reactions, but up to 150° C. for $K_2CO_3$/18-Crown-6.

Another process for preparing compounds of Formula I is by dehydrating an appropriate hydroxy derivative, as illustrated by the following equation:

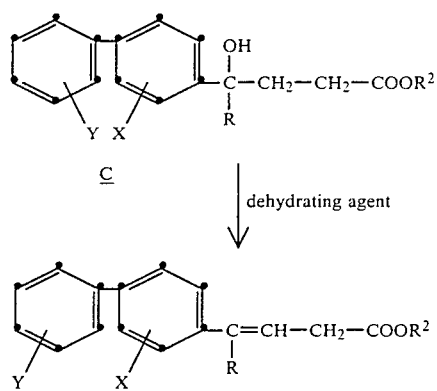

Any conventional dehydrating agent can be used for example hydrobromic acid, p-toluene sulfonic acid and the like. Generally, the reaction is carried out in a liquid reaction medium such as butanol, in the former case and xylene in the latter, at temperatures ranging from 50° to 120°.

The formula C precursor is prepared from the corresponding ketone derivative as illustrated by the following equations.

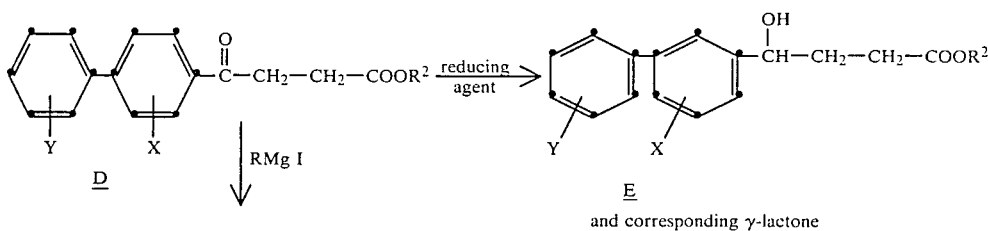

and corresponding γ-lactone

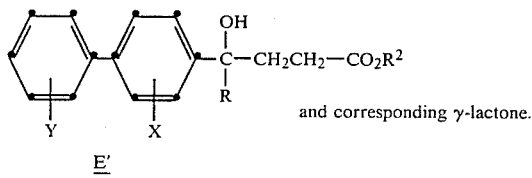

and corresponding γ-lactone.

For preparing formula E, conventional reducing agents/reaction conditions are used. Conventional Grignard reactants/conditions are used to prepare formula E'.

The preparation of precursor D involves conventional Friedel Crafts coupling of a biphenyl with an appropriate acyl halide as illustrated by the following equation:

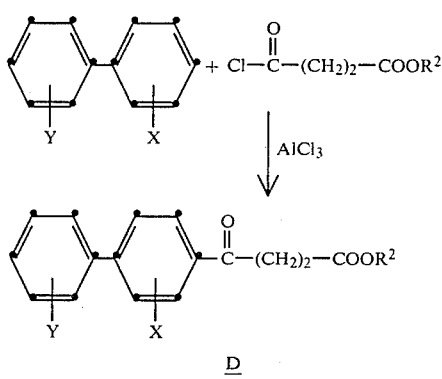

Esters of Formula I (where $R^2$ is alkyl) are prepared from the free acid (where $R^2$ is H) using conventional esterification procedures e.g. diazomethane in a suitable solvent, or an alcohol with an acid catalyst.

The following examples illustrate the preparation of the cis isomer of Formula I. All temperatures are in °C.

EXAMPLE 1

A. Wittig Approaches to 4-(4'-Biphenylyl)-3-Butenoic Acids

Cis-4-(4'-biphenylyl)-3-butenoic acid, F

To a solution of 2.66 g carboethoxyethyltriphenylphosphorane bromide in 40 mL THF was added 1.7 g $K_2CO_3$ (anhyd) and 40 mg 18-Crown-6. Then, 4-phenyl benzaldehyde (910 mg) was added. The reaction mixture was refluxed under $N_2$ for 4 hours, diluted with 200 mL diethyl ether and washed with water. The dried organic phase was concentrated and chromatographed to yield 260 mg pure cis-ethyl 4-(4'-biphenylyl))-3-butenoate, C, 80.62; H, 5.97; calc. C, 81.20; H, 6.10.

The ester was hydrolyzed by treatment of a methanolic solution with five equivalents of 1N NaOH. Acidification precipitated the product F, m.p. 174°–175° C.

EXAMPLE 2

Alternate Preparation of F

To a solution of 6.7 g $Ph_3P$, 4-phenyl benzaldehyde (2.5 g), heated to 140° C. was added acrylic acid ethyl ester (2.5 g) and heptyl alcohol (0.5 g). The reaction mixture was heated at 140°–155° for 14 hours.

The reaction mixture was poured into hexane whereupon 2.5 g $Ph_3P$ crystallized out. The balance was concentrated and chromatographed to yield 500 mg pure cis ethyl 4-(4'-biphenylyl)-3-butenoate and 2 g trans-ethyl-4-(4'-biphenylyl)-3-butenoate. The respective esters were hydrolyzed with NaOH (1N) in methanol and precipitated by acidification. cis-4-(4'-Biphenylyl)-3-butenoic acid, m.p. 172°–174°. trans-4-(4'-Biphenylyl)-3-butenoic acid, m.p. 186°–189°.

EXAMPLE 3 trans-4-(4''-fluoro-4'-biphenylyl)-3-butenoic acid G
cis-4-(4''-fluoro-4'-biphenylyl)-3-butenoic acid H To a solution of 6.7 g $Ph_3P$ 2.72 g 4''-fluoro-4-biphenylyl carboxaldehyde heated to 140° is added acrylic acid ethyl ester 2.5 g and heptyl alcohol (0.5 g). The reaction is heated at 140°–155° for 16 hours. Concentration to remove excess $Ph_3P$ followed by chromatography on silica gel permits separation of cis-4-(4''-fluoro-4'-biphenyl-yl)-3-butenoic acid ethyl ester and trans-4-(4''-fluoro-4'-biphenylyl)-3-butenoic acid ethyl ester.

Hydrolysis of the respective esters to the free acids G and H is effected by treatment with 1N NaOH in MeOH followed by precipitation with 1N HCl.

EXAMPLE 4

Friedel-Crafts Preparation of Keto Butanoic Acid Intermediate Acid

Ten grams of biphenyl was added at 0° C. to a solution containing dichloroethane (200 ml), $AlCl_3$ (25 g), and succinic anhydride (10 g).

After 45 mins. at room temperature, the solution was poured onto ice and the product isolated by filtration, (9.8 g), was 4-(4'-biphenylyl)-3-ketobutanoic acid (fenbufen).

EXAMPLE 5

Ten grams 4'-fluorobiphenyl are added at 0° C. to a solution containing dichloroethane (200 mL) $AlCl_3$ (25 g) and succinic anhydride (10 g). After 45 minutes at room temperature, the solution is poured onto ice and the product, 4-(4''-fluoro-4'-biphenylyl)-3-ketobutanoic acid is isolated by filtration.

EXAMPLE 6

General Procedure for Grignard Conversion of 3-Keto Biphenyl Butanoic Acid to Substituted 4-(4'-Biphenylyl)-3-Butenoic Acid Methyl-4-(4'-biphenylyl)-3-keto butanoate was dissolved in toluene at −40°. A molar equivalent of the respective Grignard reagent was added as a 3M solution in THF. The reaction was maintained at R.T. overnight. The organic phase was diluted with EtOAc and extracted with $H_2O$.

The organic phase was dried and concentrated. Chromatography on silica gel isolated the product as their respective γ-lactones.

The γ-lactone (7 g) was suspended in n-butanol (150 mL) and HBr (48%) (150 mL) was added. The solution was refluxed for 48 hours. At the conclusion of the reaction, the solution was diluted with water (100 mL) and extracted with EtOAc. Chromatography on silica gel permitted the isolation of a less polar (cis) isomer (20%) followed by a more polar (trans) isomer (80%) which was characterized by NMR spectroscopy. The olefinic resonance at 6.0 was a triplet representative of the $C_3$ (trans) proton whereas an olefinic resonance at 5.6 (triplet) represented the $C_3$ (cis) proton.

Hydrolysis to the corresponding free acid, methyl-4-(4'-biphenylyl)-3-butenoic acid was accomplished by treatment with 1N NaOH in MeOH at R.T. for 16 hours.

The Example 6 process may be carried out in an analogous manner starting with methyl-4(4''-fluoro-4'-biphenylyl)-3-ketobutanonate to obtain the corresponding fluoro butenoic acid.

Other alkenoic acids which may be prepared using the Example 6 process are trans-4-(4'-fluorobiphenylyl)-3-pentenoic acid, and cis-4-(4'-fluorbiphenylyl)-3-pentenoic acid.

Claims to the invention follow.

What is claimed is:

1. A pharmaceutical composition useful for treating asthma or for treating or inhibiting blood platelet aggregation comprising a pharmacologically effective amount of the cis isomer of a compound having the formula

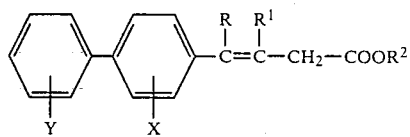

wherein
R is H or $C_1$-$C_4$ alkyl,
$R_1$ is H or $C_1$-$C_4$ alkyl,
$R^2$ is (i) hydrogen, (ii) $C_1$-$C_6$ alkyl, (iii) 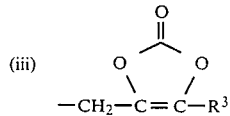

wherein $R^3$ is $C_1$-$C_6$ alkyl or aryl; or (iv) 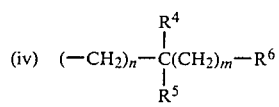

wherein
n is 0, 1, 2, or 3;
m is 0, 1, 2, or 3;
$R^4$ and $R^5$ are individually H or alkyl of 1 to 3 carbon atoms; and
$R^6$ is selected from the group consisting of
(A) a monocyclic or bicyclic heterocyclic radical containing from 3 to 12 nuclear carbon atoms and 1 or 2 nuclear hetero atoms selected from N and S with at least one being N, and with each ring in the said heterocyclic radical containing 5 to 6 members and
(B) the radical X-$R^7$ wherein X is —O—, —S—, or —NH— and $R^7$ contains up to 21 carbon atoms and is (1) a hydrocarbon radical or (2) an acyl radical of an organic acyclic or monocyclic carboxylic acid containing not more than 1 hetero atom in the ring,
Y is H, halo, $C_1$-$C_4$ alkoxy, carboxy, $C_1$-$C_6$ alkyl or azido, and
X is H, halo, $C_1$-$C_4$ alkoxy, carboxy, $C_1$-$C_6$ alkyl or azido,
and pharmaceutically acceptable salts thereof.

2. A composition of claim 1 wherein $R^2$ is H.

3. A composition of claim 1 wherein $R^2$ is H and R is $C_1$-$C_4$ alkyl.

4. A composition of claim 1 wherein $R^2$ is H and $R^1$ is $C_1$-$C_4$ alkyl.

5. A composition of claim 1 wherein $R^2$ is H and $R^1$ is H.

6. A composition of claim 1 wherein $R^2$ is H, $R^1$ is H and R is H.

7. A composition of claim 1 wherein $R^2$ is H, $R^1$ is H, R is H and X and Y are both H.

8. A method of preventing bronchoconstriction or of treating or inhibiting blood platelet aggregation in humans which comprises administering an effective amount of a compound having the formula of the compound in the composition of claim 1.

* * * * *